(12) United States Patent
Machado

(10) Patent No.: US 9,269,140 B2
(45) Date of Patent: Feb. 23, 2016

(54) IMAGE FUSION WITH AUTOMATED COMPENSATION FOR BRAIN DEFORMATION

(71) Applicant: THE CLEVELAND CLINIC FOUNDATION, Cleveland, OH (US)

(72) Inventor: Andre G. Machado, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 112 days.

(21) Appl. No.: 14/102,262

(22) Filed: Dec. 10, 2013

(65) Prior Publication Data

US 2014/0161338 A1 Jun. 12, 2014

Related U.S. Application Data

(60) Provisional application No. 61/735,101, filed on Dec. 10, 2012.

(51) Int. Cl.
| | |
|---|---|
| *G06T 7/00* | (2006.01) |
| *G06T 3/00* | (2006.01) |
| *A61B 5/00* | (2006.01) |

(52) U.S. Cl.
CPC ............ *G06T 7/0012* (2013.01); *A61B 5/0042* (2013.01); *G06T 3/0068* (2013.01); *G06T 3/0093* (2013.01); *G06T 7/0032* (2013.01); *A61B 2576/026* (2013.01); *G06T 2207/10072* (2013.01); *G06T 2207/30016* (2013.01); *G06T 2207/30096* (2013.01)

(58) Field of Classification Search
USPC ................................. 382/128–134
See application file for complete search history.

(56) References Cited

U.S. PATENT DOCUMENTS

| | | | | |
|---|---|---|---|---|
| 5,633,951 | A | * | 5/1997 | Moshfeghi ................. 382/154 |
| 5,768,413 | A | * | 6/1998 | Levin et al. ................ 382/173 |
| 5,937,083 | A | * | 8/1999 | Ostuni ....................... 382/131 |
| 6,226,418 | B1 | * | 5/2001 | Miller et al. ............... 382/294 |

(Continued)

FOREIGN PATENT DOCUMENTS

| | | |
|---|---|---|
| WO | 2008063494 A2 | 5/2008 |
| WO | 2008122056 A2 | 10/2008 |

(Continued)

OTHER PUBLICATIONS

Slomka et al., "Multimodality Image Registration With Software: State-of-the-Art", Eur J Nucl Med Mol Imaging, 2009, 36, Suppl. 1, pp. S44-S55.

(Continued)

*Primary Examiner* — Alex Liew
(74) *Attorney, Agent, or Firm* — Tarolli, Sundheim, Covell & Tummino LLP

(57) ABSTRACT

A system can include a model to represent a volumetric deformation of a brain corresponding to brain tissue that has been displaced by at least one of disease, surgery or anatomical changes. A fusion engine can perform a coarse and/or fine fusion to align a first image of the brain with respect to a second image of the brain after a region of the brain has been displaced and to employ the deformation model to adjust one or more points on a displacement vector extending through a displaced region of the brain to compensate for spatial deformations that occur between the first and second image of the brain.

19 Claims, 8 Drawing Sheets

(56) References Cited

U.S. PATENT DOCUMENTS

| | | |
|---|---|---|
| 6,374,135 B1 | 4/2002 | Bucholz |
| 7,139,601 B2 | 11/2006 | Bucholz et al. |
| 7,324,842 B2 | 1/2008 | Dale et al. |
| 7,327,138 B2 | 2/2008 | Krieg et al. |
| 7,835,778 B2 | 11/2010 | Foley et al. |
| 7,848,553 B2 | 12/2010 | Hertel et al. |
| 7,881,770 B2 | 2/2011 | Melkent et al. |
| 7,925,328 B2 | 4/2011 | Urquhart et al. |
| 7,991,450 B2 | 8/2011 | Virtue et al. |
| 8,041,088 B2 | 10/2011 | Mallya et al. |
| 8,090,429 B2 | 1/2012 | Vija et al. |
| 8,388,539 B2* | 3/2013 | Yamamoto et al. ........... 600/443 |
| 2005/0101855 A1* | 5/2005 | Miga et al. .................... 600/407 |
| 2005/0141757 A1* | 6/2005 | Ayache et al. ................. 382/128 |
| 2006/0034545 A1* | 2/2006 | Mattes et al. .................. 382/294 |
| 2007/0003117 A1* | 1/2007 | Wheeler et al. ............... 382/128 |
| 2007/0003118 A1* | 1/2007 | Wheeler et al. ............... 382/128 |
| 2007/0014448 A1* | 1/2007 | Wheeler et al. ............... 382/128 |
| 2007/0019846 A1* | 1/2007 | Bullitt et al. .................. 382/128 |
| 2007/0160277 A1* | 7/2007 | Slabaugh et al. ............. 382/128 |
| 2010/0036233 A1* | 2/2010 | Zhu ...................... A61B 6/5247 600/410 |
| 2014/0161338 A1* | 6/2014 | Machado ...................... 382/131 |

FOREIGN PATENT DOCUMENTS

| | | |
|---|---|---|
| WO | 2011091218 A1 | 7/2011 |
| WO | 2012155964 A1 | 11/2012 |

OTHER PUBLICATIONS

International Search Report and Written Opinion, mailed Mar. 27, 2014, pp. 1-11.

* cited by examiner

IMAGE FUSION WITH AUTOMATED COMPENSATION FOR BRAIN DEFORMATION

CROSS-REFERENCE TO RELATED APPLICATION

This application claims the benefit of U.S. Provisional Patent Application 61/735,101 filed on Dec. 10, 2012, and entitled IMAGE FUSION WITH AUTOMATED COMPENSATION FOR BRAIN DEFORMATION, the entirety of which is incorporated by reference herein.

TECHNICAL FIELD

This disclosure relates to image fusion with automated compensation for brain deformation.

BACKGROUND

Image fusion has become a common term used within medical diagnostics and treatment. The term is used when multiple patient images are registered and overlaid or merged to provide additional information. Fused images may be created from multiple images from the same imaging modality, or by combining information from multiple modalities, such as magnetic resonance image (MRI), computed tomography (CT), positron emission tomography (PET), and single photon emission computed tomography (SPECT), for example. In radiology and radiation oncology, these images serve different purposes. For example, CT images are used more often to ascertain differences in tissue density while MRI images are typically used to diagnose brain tumors.

For accurate diagnoses, radiologists must integrate information from multiple image formats. Fused, anatomically-consistent images are especially beneficial in diagnosing and treating cancer. Many companies have recently created image fusion software for both improved diagnostic reading and for use in conjunction with radiation treatment planning systems. With the advent of these new technologies, radiation oncologists can take advantage of intensity modulated radiation therapy (IMRT). Being able to overlay diagnostic images onto radiation planning images results in more accurate IMRT target tumor volumes, for example.

Another area where one type of image is fused on to another includes the uses of atlases in fusion. For instance, medical images can vary significantly across individuals due to people having organs of different shapes and sizes. Therefore, representing medical images to account for this variability is crucial. A popular approach to represent medical images is through the use of one or more atlases. Here, an atlas refers to a specific model for a population of images with parameters that are learned from a training dataset. One example of an atlas is a mean intensity image, commonly referred to as a template. However, an atlas can also include richer information, such as local image statistics and the probability that a particular spatial location has a certain label. New medical images can be mapped to an atlas, which has been tailored to the specific application, such as segmentation and group analysis. Mapping an image to an atlas usually involves registering the image and the atlas. This deformation can be used to address variability in medical images.

SUMMARY

This disclosure relates to image fusion with automated compensation for tissue deformation.

In one example, a system can include a model to represent a volumetric deformation of a brain corresponding to brain tissue that has been displaced or shifted by at least one of disease, surgery or anatomical changes. A fusion engine can perform a coarse fusion to align a first image of the brain with respect to a second image of the brain after a region of the brain has been displaced and to employ the model to adjust one or more points on a displacement vector extending through a displaced region of the brain to compensate for spatial deformations that occur between the first and second image of the brain.

As another example, a method can include determining an initial volume for at least one selected anatomic region in a first three-dimensional brain image for a patient. Another volume for the at least one selected anatomic region can be determined in a second three-dimensional brain image for the patient. Shrinkage or growth factors can be computed from the first three-dimensional brain image based on a difference between the initial volume and the another volume for the at least one selected anatomic region. A mapping between the first and second three-dimensional brain images can be generated based on the computed shrinkage or growth factors and at least one volume parameter for the brain that compensates for distortion between the first and second three-dimensional brain images.

As yet another example, a method can include accessing a first image data of an anatomical feature and second image data of the anatomical feature. A non-rigid alignment can be performed between the first image data and the second image data. A vector field mapping can be determined based on the non-rigid alignment to provide displacement data to a user regarding displacement between the first image and the second image data.

DETAILED DESCRIPTION

This disclosure relates to systems and methods to improve image fusion technologies where non-homogenous compensation methods are applied to images having post-procedural brain deformations to improve overall fusion performance. The approach disclosed herein can employ a workflow that can initially involve a coarse fusion that can be performed utilizing various brain and spatial morphological and volumetric parameters before, during and/or after medical, diagnostic or surgical procedures have been performed. In some examples, coarse fusion of the overall brain can be initially accomplished by fusing the skull, ventricular volume as well as the subarachnoid volume between images of the patient's brain and other brain images or a common image or atlas framework. Fiducial markers, such as identifiable landmarks, in the brain can then be applied to the coarse fusion to further compensate and adjust for other distortions that may have occurred. Such fusion can be applied to images from the same or different imaging technologies, such as Computed Tomography (CT) and Magnetic Resonance Imaging (MRI).

As a further example, the methods can be applied to preoperative and post-operative imaging to enable more accurate comparisons between such images and account for anatomical deformations that may have occurred, such as due to the respective procedures or other patient conditions (e.g., trauma, lesions or the like). In another example, the compensation methods can be utilized to improve the fusion of atlases with brain images for patients that have undergone surgical procedures or otherwise experience deformations in cranial and intracranial structures. For instance, the fusion process enables more accurate registration of the atlas and the brain image by adjusting the atlas based on the computed resultant deformation. The fusion can be further improved by utilizing additional landmarks in a target region of interest, thereby producing a more accurate brain atlas for the patient. As a result, the resulting brain atlas can further lead to improved accuracy in surgical procedures (e.g., stereotactic procedures) in which the target ROI resides in a spatially deformed region.

Figure 1:
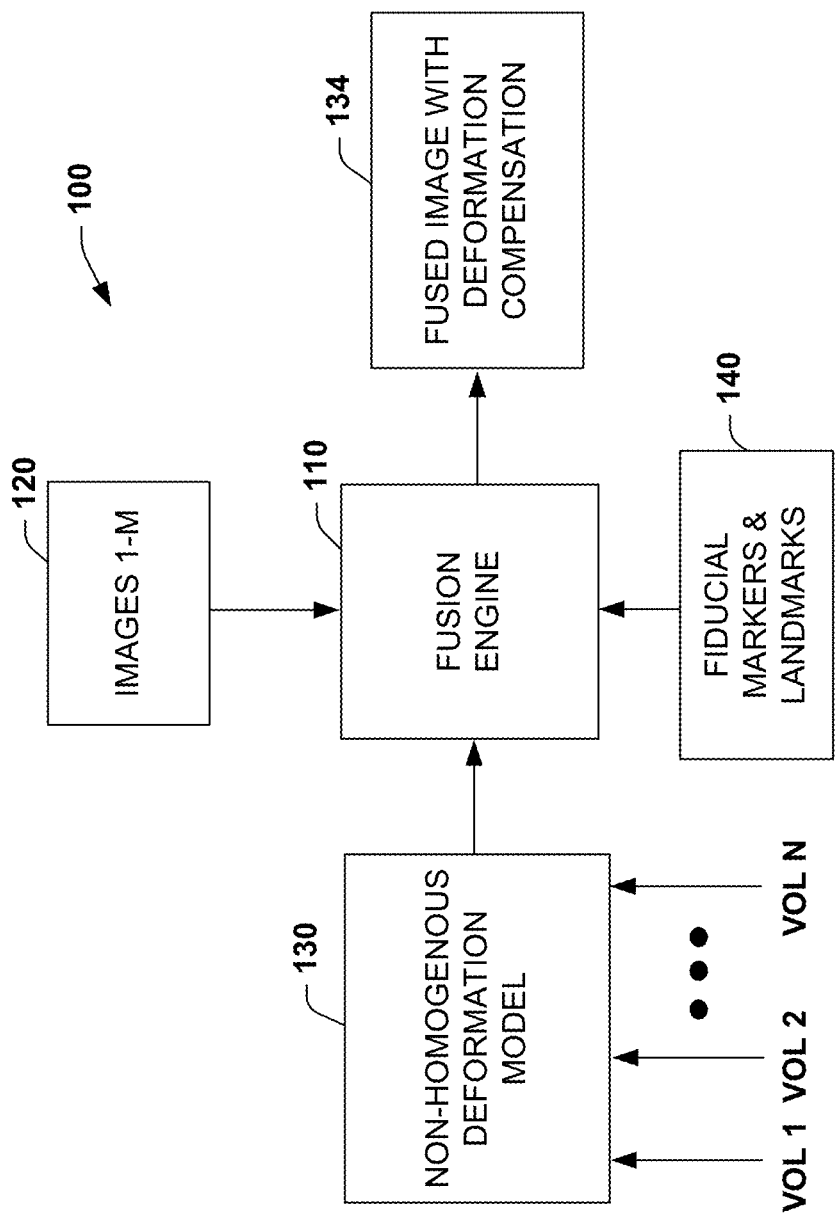
FIG. 1 illustrates an example of a system to perform image fusion while compensating for anatomical deformations in images.

FIG. 1 illustrates an example of a system 100 that performs image fusion while compensating for deformations in images that may have occurred due to operative procedures or other localized anatomical changes. In the example of FIG. 1 and other examples disclosed herein, image fusion is often discussed in the context of images for a patient's brain pre- and post-procedure. However, it is to be understood that image fusion is applicable to other images of a given anatomical structure that can experience one or more localized deformations for any reasons, whether or not a procedure has been performed. Thus, as used herein, a post-procedure image is intended to be interchangeable with post-deformation image, meaning that at least one of the images being fused has an anatomical deformation relative to at least another of the images being fused regardless of what might have caused such deformation. Post-procedure is typically used herein in the description and claims simply for sake of consistency and not by way of limitation unless explicitly specified.

The system 100 includes a fusion engine 110 that processes various images 120 and applies non-homogenous compensation methods to the images having post-procedural brain deformations to improve overall fusion performance. Fusion involves overlaying and co-registration (e.g., alignment) of various images 120 by the fusion engine 110 (e.g., software and/or processor performing fusion) and/or other data where some of the images may involve preoperative and postoperative views of the brain. Such fused images can be generated as a magnetic resonance image (MRI), computed tomography (CT), positron emission tomography (PET), and single photon emission computed tomography (SPECT), to name but a few examples. In some examples, fused images can be generated at 134 by the fusion engine 110 between the same imaging modalities (e.g., preoperative/postoperative MRI on MRI) or can occur via different imaging modalities (e.g., preoperative/postoperative MRI on CT). In other examples, one or more of the images 120 could be an MRI or CT image and another type of image could be an atlas of the brain (e.g., coordinate point mapping of the brain), wherein the atlas image 120 is to be registered with a postoperative brain image 120.

During (e.g., perioperatively) and after a surgical procedure on the brain, image compensation can be applied to perioperatively acquired images 120 and can initially involve a coarse fusion (e.g., rigid alignment between images) to account for brain deformations and adjust brain images accordingly. As used herein, the term "coarse" relates to an initial adjustment of a deformed image wherein volume parameters computed for the brain are used to adjust the respective image (e.g., increase or decrease a deformed boundary region in an image based on volumetric computations). The coarse fusion can be performed by a deformation model 130 (also referred to as a deformation model). The deformation model 130 utilizes various brain volumetric parameters, shown as Vol 1 through Vol N, N being a positive integer, which accounts for volume differences in brain physiology before and after surgical procedures have been performed. For example, the deformation model 130 can be generated by analyzing a plurality preoperative and postoperative image sets of brain images that have been captured before procedures have taken place and after the respective procedures. The deformation model 130 can model volumetric differences that are observed over the plurality of image sets. This can include the computation of vector fields having a magnitude and direction with respect to the preoperative and postoperative images. The deformation model 130 can also consider the type of procedure performed, the angle and depth of insertion of a given surgical probe, and how surgical deformations can change over time. A comparison of the pre- and post-surgical volumes can be employed to compute growth or shrinkage coefficients that can be stored as the volumetric parameters. In one example, the volumetric parameters can include a ventricular region and, in another example, such parameters can include a subarachnoid region. The coefficients and other volumetric parameters can be utilized to fit volumes of interest (e.g., ventricles and cortex) of the atlas to the patient's anatomy.

The fusion engine 110 can also employ fiducial markers (e.g., image notations or points of interest) and/or known landmarks 140 on the brain image 120 that has undergone the coarse fusion to further compensate and adjust for other distortions that may have occurred during and/or after the procedure, corresponding to a fine fusion (e.g., non-rigid alignment). The fiducial markers and landmarks 140 can be applied manually by an operator and/or can be applied automatically (e.g., by an algorithm or learning system). Such compensation can be applied to various imaging technologies as noted above, wherein the compensation methods can be applied to perioperative imaging to enable more accurate comparisons between such images and account for deformations that may have occurred due to the respective procedures. In another example, the compensation methods can be utilized to improve the registration of atlases on to brain images 120 that have undergone surgical procedures or otherwise experienced one or more anatomical deformations, wherein the compensation by the fusion engine 110, deformation model 130, and markers 140 enables more accurate overlay of the atlas on to the brain image by adjusting the atlas in accordance with the resultant deformation.

In some examples, the system 100 can be employed to fuse brain imaging of patients before and after a mass occupying lesion has occurred. As used herein, a mass occupying lesion can refer to a presence or absence structure or fluid that cause a distortion or deformation of one or more spatial region of the brain. The distortion or deformation can be static or it may evolve over time and be tracked by a sequence of images acquired at different times. The system 100 may be used for several surgical and non-surgical uses but for purposes of brevity, examples of stereotactic procedures such as deep brain stimulation are used to explain applicable methods. The fusion engine 110 can be employed to co-register images 120 acquired intraoperatively or postoperatively, including before and after pneumocephalus, for example, has occurred. Additional imaging can be performed to track deformation resulting from the pneumocephalus. The resulting atlas that is fused to the perioperative image(s) can be utilized to aid in accurate placement of deep brain stimulation leads or related procedures.

The system 100 can generate image fusion with modern methodologies to create a best fit fusion between the imaging of the patient's brain acquired before and after deformation caused by a mass occupying lesion has occurred, for example, such as pneumocephalus. Multiple internal anatomical landmarks 140 can also be utilized to improve the best fit function in the overall fusion. Additional landmarks 140 may be used to improve images further in a particular region (e.g., volume) of interest so that stereotactic targeting may be less corrupted. Some of these landmarks 140 can also be used to verify that the fusion is accurate before clinical decisions are made.

The system 100 can be employed to improve the accuracy of procedures such as stereotactic procedures (e.g., biopsy, deep brain stimulation or other probe placement) or brain tumor surgery or any other procedure that requires comparing an intraoperative image or postoperative image with a preoperative image. In the example of deep brain stimulation, compensation methods described herein can be used to compare/merge/fuse CT scans or MRIs, for example, acquired during surgery or after surgery with preoperative imaging.

As mentioned above, one problem that can be addressed by the system 100 is related to mass occupying lesions in or around the patient's brain. Examples of lesions can include pneumocephalus, tumors or the like. Such lesions can be static although more likely the lesions can shift and/or grow causing resulting displacement of the brain relative to the lesion. As used herein, tissue displacement generally results by the application or removal of force, for example, the application or removal of a surgical probe. Displacement can also include shifting which can occur when an initial tissue deformation shifts or moves over time. For example, images 120 acquired intraoperatively, the brain can be displaced by pneumocephalus. This imposes difficulties when comparing to preoperative imaging, which is the imaging used to select the target site to place a probe since the site may have shifted non-linearly relative to a stereotactic coordinate system. One of the purposes of acquiring the intraoperative imaging is to assess if the probes have been placed in the target as intended. However, if the target is displaced by pneumocephalus, the intraoperative imaging may provide a misleading impression of where the probe is located (e.g., right or wrong), reducing the value of intraoperative imaging. By applying the compensation and fusion methods described herein to images 120 by the fusion engine 110, deformation model 130, and markers 140, intraoperative imaging can be employed to better understand if the probes are well placed or not and be utilized with greater accuracy to stereotactically guide implantation with a brain atlas or patient image.

In another aspect, the fusion engine 110 can process at least one image event that includes at least one of a location of a fiducial marker, a foreign body inserted in the brain, or an anatomical structure after anatomical displacement. The image event can be correlated or co-registered with the corresponding location in the images acquired before the anatomical displacement occurred or after the anatomical displacement has resolved partially or completely, for example. The fusion engine 110 can compensate for a structural shift that includes a brain shift associated with surgical procedures. In another example, the fusion engine 110 determines an initial volume for at least one selected anatomic region in a first three-dimensional brain image for a patient and determines another volume for the selected anatomic region in a second three-dimensional brain image for the patient.

The fusion engine 110 can compute shrinkage or growth factors from the first three-dimensional brain image based on a difference between the initial volume and the another volume for the at least one selected anatomic region and generates a mapping between the first and second three-dimensional brain images based on the computed shrinkage or growth factors and at least one volume parameter for the brain to provide feedback that compensates for distortion between the first and second three-dimensional brain images. This can also include utilizing one or more fiducial markers or landmarks to characterize inhomogeneities in anatomy or inhomogenities in a vector of displacement to align images from a digitized atlas and a brain image, for example.

Current technologies generally can only match well/fuse well images from the same patient, such as CT scan to MRI that are substantially equivalent. These images do not fuse well when one of the images has a mass occupying lesion. Current algorithms and work flow presumes that the anatomy is the same between the two. The system 100 can solve this limitation however, and allow for intraoperative imaging and postoperative imaging to be combined and compared to preoperative imaging. As noted above, the system 100 can perform a workflow in which coarse fusion of the overall brain can be initially accomplished by fusing the skull volume, extracranial structure, intracranial volume and structures and ventricular volume as well as the subarachnoid volume, for example. Then, additional distortions can be accounted for with internal fiducial markers and well-known landmarks 140, such as those residing in a region of interest. The landmarks 140 can be used to compensate for the inhomogeneities of structural displacement, which may need to be accounted for. In another example, the fusion engine 110 and deformation model 130 can be utilized in combination with surgical planning software and/or hardware platforms so that the fused images (intraoperative-postoperative-preoperative) can be used to inform surgery decision-making or post-surgical evaluation. For example, a location and/or trajectory in three-dimensional space can be computed from the fused image to accounts for anatomical deformation.

In another example, the system 100 can be employed to fuse patient brain images a brain atlas and vice-versa. In some examples, the resulting fused image 134 can be used for stereotactic targeting of anatomical sites, such as cortical or subcortical structures that cannot be well visualized in the patient's brain imaging. There are current clinical platforms that attempt at performing such procedures with inefficient and inaccurate fusion protocols. These methods are based on atlas outlines and may be discredited by stereotactic and functional neurosurgeons because of the high-risk that the overlaid atlas does not match well with the actual patient's anatomy. The system 100 solves these problems by utilizing image fusion with non-homogeneous methodologies to create a best fit fusion between the patient's brain imaging and the atlas based on multiple fiducial points as well as a technique for volume fusion of the ventricular as well as subarachnoid spaces. Multiple internal landmarks can also be utilized to improve the best fit in the overall fusion between the image(s) and the atlas. Additional landmarks may be used to improve the fusion further in the region of interest so that stereotactic targeting based on the fused atlas brain can be more accurate. Some of the landmarks can also be used by the condition to verify that the fusion is accurate before clinical decisions are made and/or a stereotactic procedure is performed.

Another problem with current technologies is that the current atlases are designed for adjusting to the patient's brain in two dimensions and it assumes that the atrophic changes and differences between the patient's brain and the atlas are homogeneous when they are often not, as illustrated below with respect to FIG. 2. These differences are variable and inhomogeneous and in order to account for such, multiple layers of fusion are utilized. The system 100 provides a method in which coarse fusion of the overall brain can be initially accomplished by fusing images of the ventricular volume as well as the subarachnoid volume with atlas images during a rigid alignment described below with respect to FIG. 5. A non-rigid alignment can subsequently be performed between the rigid alignment and the preoperative image. Then, additional distortions can be accounted for with internal fiducial markers and well-known landmarks. Depending on the target of interest, the atlas-based fusion can be further improved with additional landmarks in or adjacent that same target area.

Figure 2:
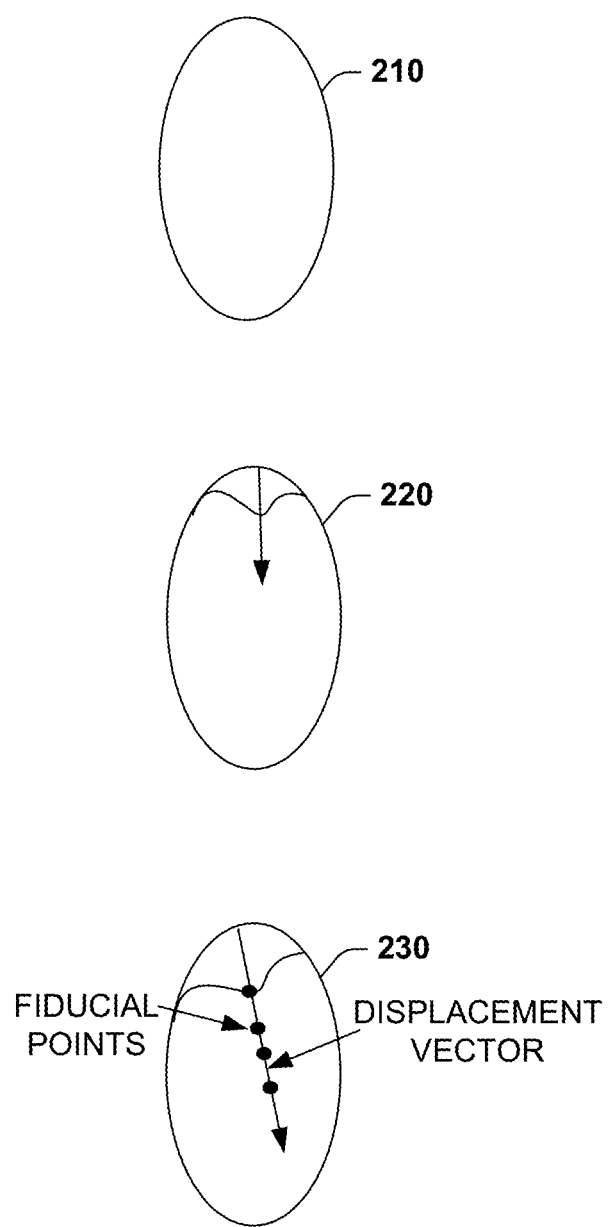
FIG. 2 illustrates an example of a brain deformation in simplified brain images demonstrating a determination of displacement vectors and fiducials.

FIG. 2 illustrates an example of brain deformation in simplified diagrams representing brain images having different mass occupying lesions as well as the determination of displacement vectors and fiducials. At 210 of FIG. 2, a preoperative image of a brain is shown. At 220, after a procedure has occurred, a direction arrow shows a displacement vector in the brain image. Such displacement could occur for example as a bubble of air is released from an access opening in the cranium, a pneumocephalus, for example. The displacement vector can extend through an area of maximum deformation, for example. At 230, a further non-homogeneous nature of the displacement depicted at 220 is shown. For example, a pneumocephalus within the cranium may have moved during a procedure causing the brain to shift (e.g., deform) in a non-homogeneous manner. A displacement vector having a direction and magnitude can be calculated based on a current level of deformation due to the distortion and depicted along the path, shown as a displacement vector. The displacement vector can be calculated in three dimensions by utilizing a non-linear displacement function along the vector. As shown, after the displacement vector, which can be a non-linear function, has been determined for a given mass occupying lesion and indicating one or more directions and magnitude for the displacement, fiducial points can be located (e.g., manually and/or automatically) along the displacement vector to further reduce distortions in the image. For example, the fiducial points can correspond to voxels in three dimensions.

In some examples, a volume of the bubble (pneumocephalus) can be calculated and a long axis thereof be computed. The displacement vector can be computed as being perpendicular to the long axis of the bubble. A gradient of the displacement along the displacement vector can also be calculated. The gradient and the displacement vector can be used to calculate a corresponding displacement for unknown points in the region of interest. For example, the fiducial marker can be employed to stretch or reduce boundary points in the brain image along the displacement vector and compensate for the displacement of the brain along the vector. In addition to the fiducials, landmarks within the brain can further be employed to reduce or increase boundary areas in order to further quantify the anatomical distortion. The method of FIG. 3, as disclosed herein, will further highlight the utilization of displacement functions, vectors, fiducials, and landmarks to mitigate displacement distortion in postoperative or intraoperative brain images.

Figure 3:
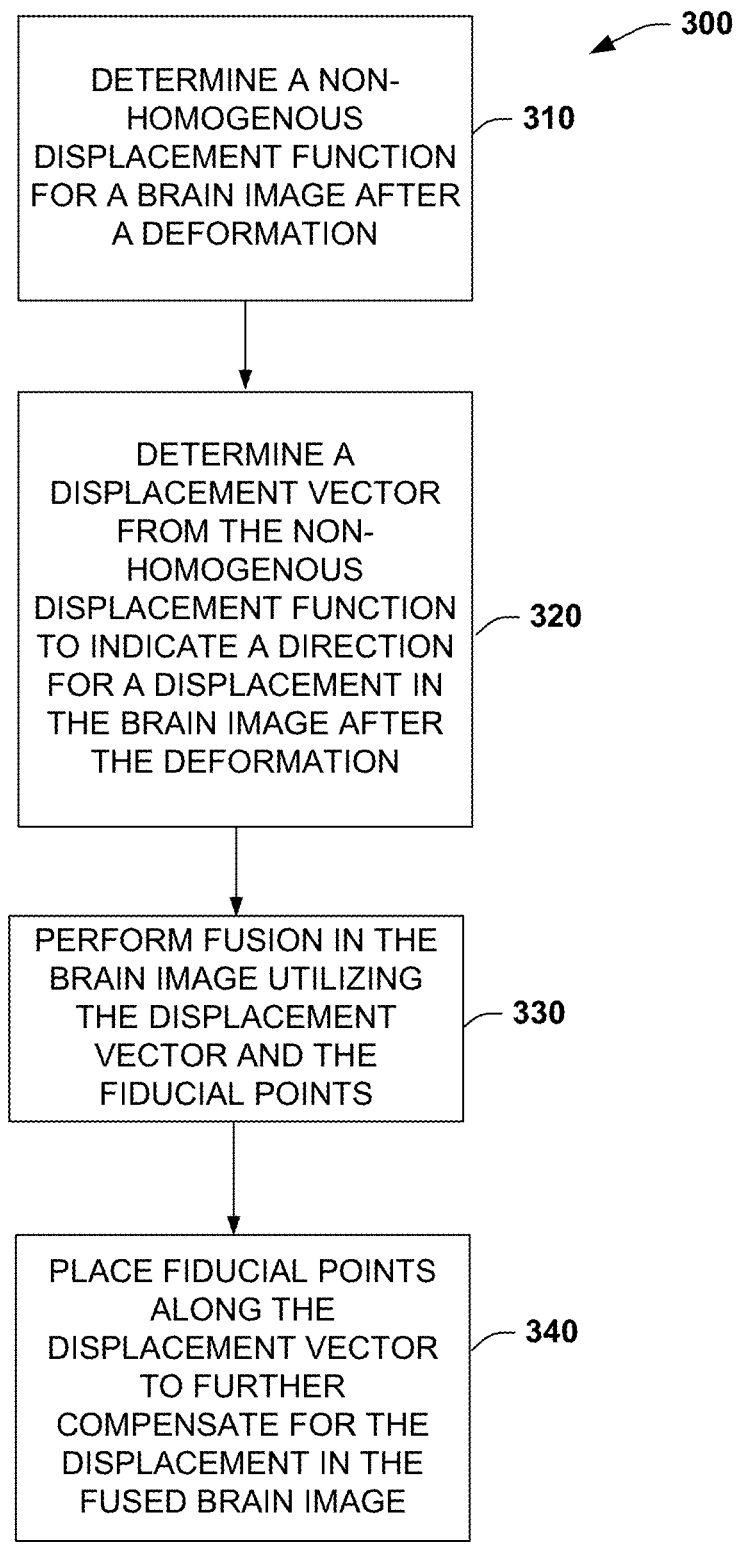
FIG. 3 illustrates an example method for performing image fusion between anatomical images taken before, during, and after operative procedures.
Figure 4:
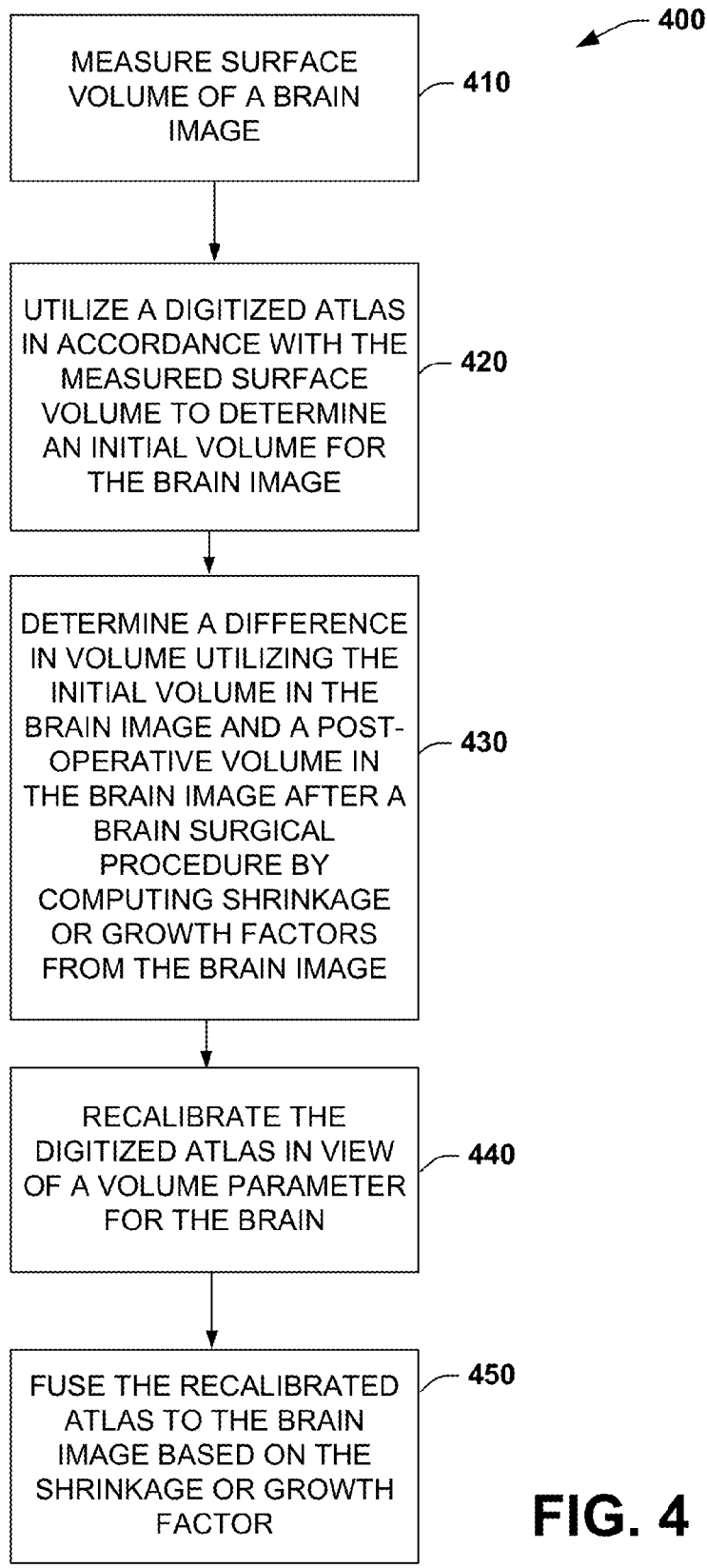
FIG. 4 illustrates an example method for performing image fusion between an atlas image and brain images taken before, during, and after operative procedures.
Figure 7:
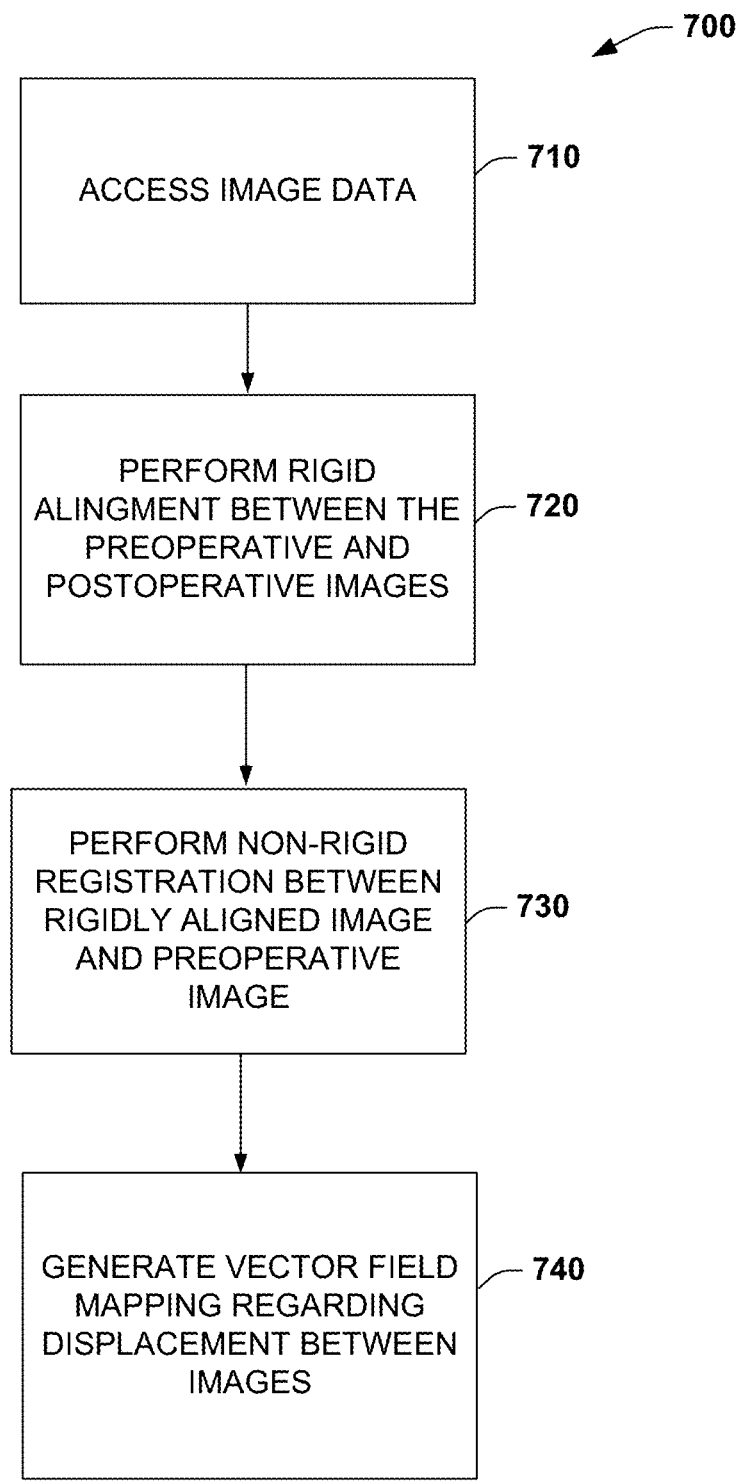
FIG. 7 illustrates an example method for performing displacement mapping via rigid and non-rigid alignment or preoperative and postoperative images.

In view of the foregoing structural and functional features described above, example methods will be better appreciated with reference to FIGS. 3, 4, and 7. While, for purposes of simplicity of explanation, the methods are shown and described as executing serially, it is to be understood and appreciated that the methods are not limited by the illustrated order, as parts of the methods could occur in different orders and/or concurrently from that shown and described herein. Such methods can be executed by various components configured as executable instructions stored in a computer memory (e.g., one or more non-transitory computer readable media) and executed by a processor, for example.

FIG. 3 illustrates an example method 300 for performing image fusion between brain images taken before, during, and after operative procedures. At 310, the method 300 includes determining a non-homogenous displacement function for a brain image (e.g., via deformation model 130 of FIG. 1), such as after deformation (e.g., following performance of a surgical procedure). At 320, the method 300 includes determining a displacement vector from the non-homogenous displacement function to indicate a direction for a displacement in the brain image after the deformation has been performed (e.g., via deformation model 130 of FIG. 1). At 330, the method 300 includes performing a coarse fusion in the brain image utilizing the displacement vector (e.g., fusion engine 110 of FIG. 1). At 340, the method 300 includes placing fiducial points along the displacement vector to further compensate for the displacement in the brain image (e.g., via fiducial markers and landmarks 140 of FIG. 1). The method 300 can also include utilizing landmarks in the brain image in accordance with the fiducial points to further compensate for the displacement in the brain image. This can include fusing preoperative, intraoperative, and postoperative brain images. The method 300 can also include fusing preoperative, intraoperative, and postoperative brain images with an atlas, for example.

FIG. 4 illustrates an example method 400 for performing image fusion between an atlas image and brain images taken before, during, and after operative procedures. At 410, the method 400 includes measuring surface volume of a brain image (e.g., via fusion engine 110 of FIG. 1). At 420, the method 400 includes utilizing a digitized atlas in accordance with the measured surface volume to determine an initial volume for the brain image (e.g., via fusion engine 110 of FIG. 1). At 430, the method 400 includes determining a difference in volume utilizing the initial volume in the brain image and a post-operative volume in the brain image after a brain surgical procedure by computing shrinkage or growth factors from the brain image (e.g., via deformation model 130 of FIG. 1). At 440, the method 400 includes recalibrating the digitized atlas based on a volume parameter for the brain (e.g., via deformation model 130 of FIG. 1). At 450, the method 400 includes fusing the recalibrated atlas to the brain image utilizing the shrinkage or growth factor (e.g., via fusion engine 110 of FIG. 1). The method 400 can also include utilizing one or more landmarks to align the digitized atlas and the brain image following alignment of one or more volume of interest. This can include increasing or decreasing target areas in the brain image via fiducial markers that are placed on to the brain image.

Figure 5:
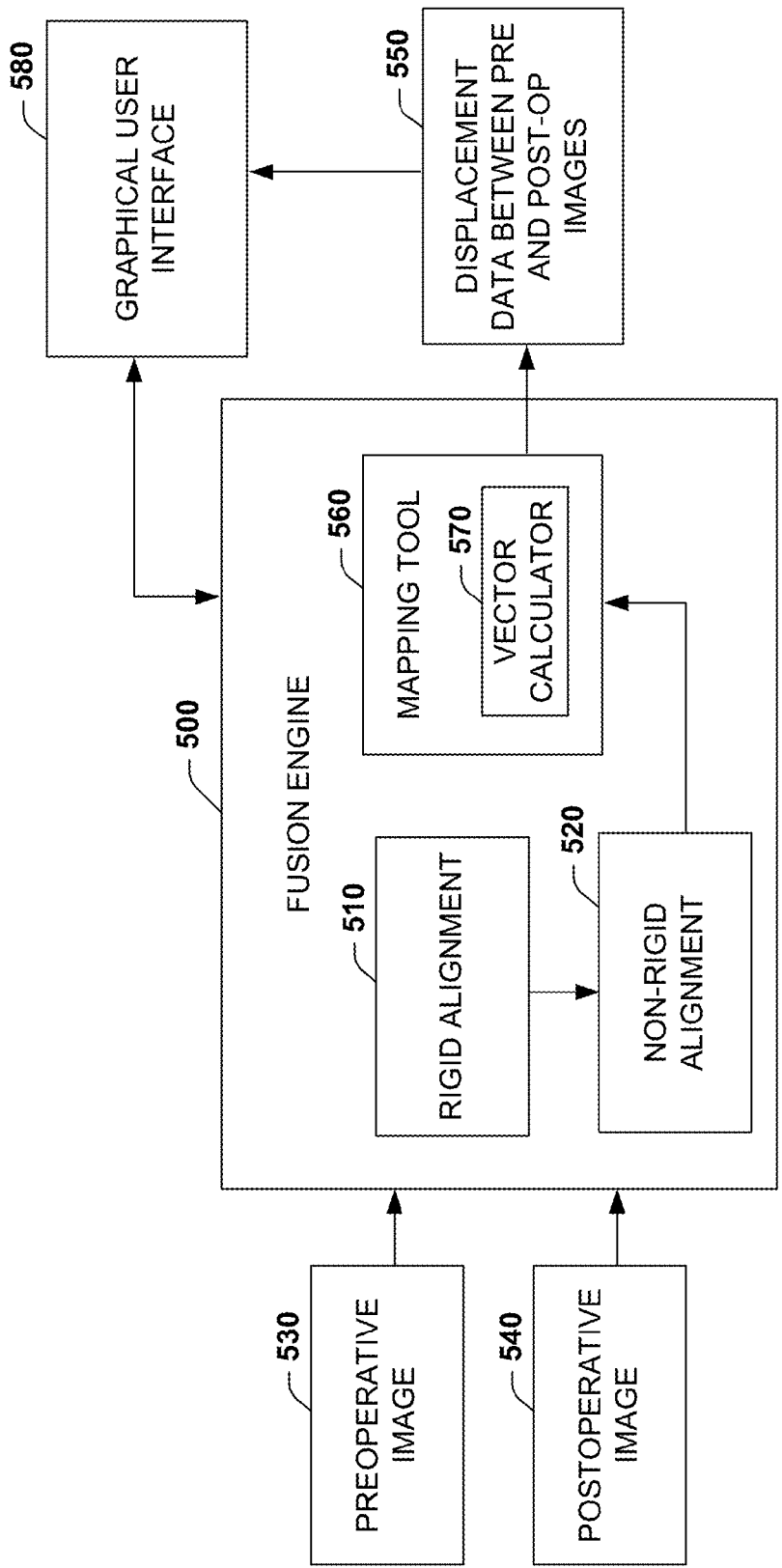
FIG. 5 illustrates an example of fusion engine to perform rigid and non-rigid alignment between preoperative and postoperative images to generate displacement feedback with respect to a selected point within the images.

FIG. 5 illustrates an example fusion engine 500 that performs rigid alignment 510 and non-rigid alignment 520 between different images of common anatomical structure. In the example of FIG. 5, one of the images is demonstrated as a preoperative image 530 (also referred to as preop image) and another image is demonstrated as a postoperative image 540 (also referred to as post op image and/or intraoperative image). The fusion engine 500 is configured to generate displacement data 550 with respect to one or more points (e.g., up to all pixels or voxels) within the images 530 and 540.

The fusion engine 500 receives the preoperative image 530 and the post operative image 540 and initially performs the rigid alignment 510 between the two images. The rigid alignment 510 can also be considered a coarse fusion as previously described. The rigid alignment 510 is utilized to provide a general orientation between the preoperative image 530 and the postoperative image 540 where a subset of image points (e.g., 16 points located at the exterior of the respective images) may be used to generally align the two images with respect to each other (e.g., align images in the same general direction and in the same general image space). In one example, the postop image 540 may have a deformation due to a surgical procedure such as an insertion of a probe or removal of tissue (e.g., tumor) as previously described. After the rigid alignment 510, the fusion engine 500 can perform the non-rigid alignment 520 where non-linear vectors and transformations can be generated to facilitate an alignment between the preop image 530 and the postop image 540. The non-rigid alignment 520 can also be considered a fine fusion as previously described.

After the non-rigid alignment 520, a mapping tool 560 determines a displacement vector which represents a mapping between where a selected point was in the preop image 530 to its displaced location in the postop image 540. The mapping tool 560 can include a vector calculator 570 to compute the displacement vector. As shown, the displacement data 550 generated by the mapping tool 560 can be provided to a graphical user interface (GUI) 580 to provide feedback to the user regarding the selected point. The GUI 580 can enable the user to select a plurality of differing points of interest on the preoperative image 530, post-operative image 540, and/or fused image where the vector calculator 570 of the mapping tool 560 computes updated displacement data 550 based on the selected point received from the GUI 580.

The selected points can be identified manually (e.g., via fiducial points and landmarks previously described) and/or automatically by mapping between dynamically determined anatomical features. This could include comparing features to a preop and postop grid for example and determining a plurality of displacement vectors for a plurality of points with respect to the grids. The mapping tool 560 and vector calculator 570 can compute the displacement data 550 to provide a displacement vector for each pixel or voxel in the fused image that specifies a magnitude and direction by which each such pixel or voxel has shifted between the images 530 and 540. This magnitude and direction further can be provided as a corresponding vector in three dimensional space such as a stereotactic coordinate system for the patient. After the respective mapping by the mapping tool 560, the displacement data 550 can provide feedback via the GUI 580 to indicate how much a given anatomical point or feature has shifted after a surgical procedure and/or how a given deformation has shifted over time. Such feedback thus can be employed to accurately locate a given anatomical feature or determine a trajectory that has shifted due to the anatomical deformation and further be utilized for surgical intervention and/or analysis.

Additionally, the fusion engine 500 can employ one or more predictive models to predict anatomical movement over time. For example, image databases (not shown) can be analyzed to determine how a given type of deformation may shift over time. As an example, a deformation bubble (e.g., pneumocephalus) can be analyzed over time from a plurality of images for various patients to observe and mathematically describe how a given bubble may shift over time and/or as further surgical procedures commence. This can include analyzing parameters that can include probe insertion angles, anatomical shapes, anatomical procedures employed, anatomical instruments employed, and so forth to determine how a given bubble is initially formed and how the bubble may shift as a function of time and related parameters. Various time/displacement shift vectors can then be generated to update the model. The model can then be employed by the fusion engine 500 to update the displacement data 550 over time to provide a predicted deformation of how an anatomical structure (e.g., for each pixel or voxel of the structure) may shift over a given time period.

By way of example, the vector calculator 570 can be configured to generate the displacement data 550 as including a volume vector field that indicates on a per-voxel basis the direction and magnitude that each respective voxel moves between each of the respective images 530 and 540. For instance, the volume vector field can indicate the "aligned" (rigid) and "registered" (non-rigid) volumes. As used herein, a voxel refers to a single sample, or data point, on a regularly spaced three dimensional grid. This data point can consist of a single piece of data, such as an opacity, or multiple pieces of data, such as a color in addition to opacity, for example.

As a further example, the field vector calculator 570 can provide a 3D floating point field with various colors representing movement (e.g., magnitude and direction). For example, gray areas can be used to indicate no movement (although darker or lighter grays can indicate uniform movement in all 3 axes) and colors can be used indicate movement predominantly along one or two axes. For instance, stronger colors can indicate a greater amount of movement due to deformation. An image corresponding to the field vector can be provided as an output map of the patient anatomy to visualize the computed deformation. Different combinations of color scales can be utilized to depict different features of the field vector to help the user understand that extent and direction of deformation that has occurred. Analysis of similar trends over multiple similar image sets for one or more patients could be used to generate the deformation model, previously described. The fusion engine 500 can interpret files in such a manner as to obtain a displacement between the preoperative, postoperative, and intraoperative images on a per-pixel and/or per voxel basis.

One intermediate aspect of the registration process is to optimally align each intraoperative (e.g., bubble) scan 540 to each preoperative (e.g., normal) scan 530, creating a re-sampled, registered bubble dataset which, ideally, minimally differs from the normal dataset. After registration, the vector field calculator 470 of the mapping tool 560 can determine displacement vectors between the respective images. Various alignment tools can be employed to perform image alignment and/or registration. One commercially available tool (e.g., the NiftyReg application developed at the University College London) employs command line parameters to control behavior and execution of image alignment. Other tools may employ a configuration file to control behavior and execution of image alignment. In general with respect to a bubble deformation in the post op image 540, the fusion engine 500 performs the rigid alignment 510 of the bubble image to normal datasets to produce a "rigid" transform representing the optimal rigid mapping of the bubble dataset to the normal dataset.

Using the "rigid" transform produced by the rigid alignment 510, the fusion engine 500 re-samples (e.g., transforms) the bubble dataset, generating a new "aligned" dataset in which the bubble data has been rotated and/or translated to maximally overlap the normal dataset, and re-sampled onto a 3D lattice/grid similar to the normal dataset. The fusion engine 510 then performs the non-rigid (e.g., non-linear) registration 520 of the new, aligned dataset produced at 510 to the original (e.g., normal) dataset, creating a "non-rigid" transform. Using the "non-rigid" transform produced at 520, the fusion engine 500 creates a new "registered" dataset in which the each of the pixels or voxels are re-sampled onto a 3D lattice/grid of the normal, original dataset corresponding to the image 530. From the registered data set, the mapping tool 560 can then generate displacement vectors between selected points in the post op image 540.

Figure 6:
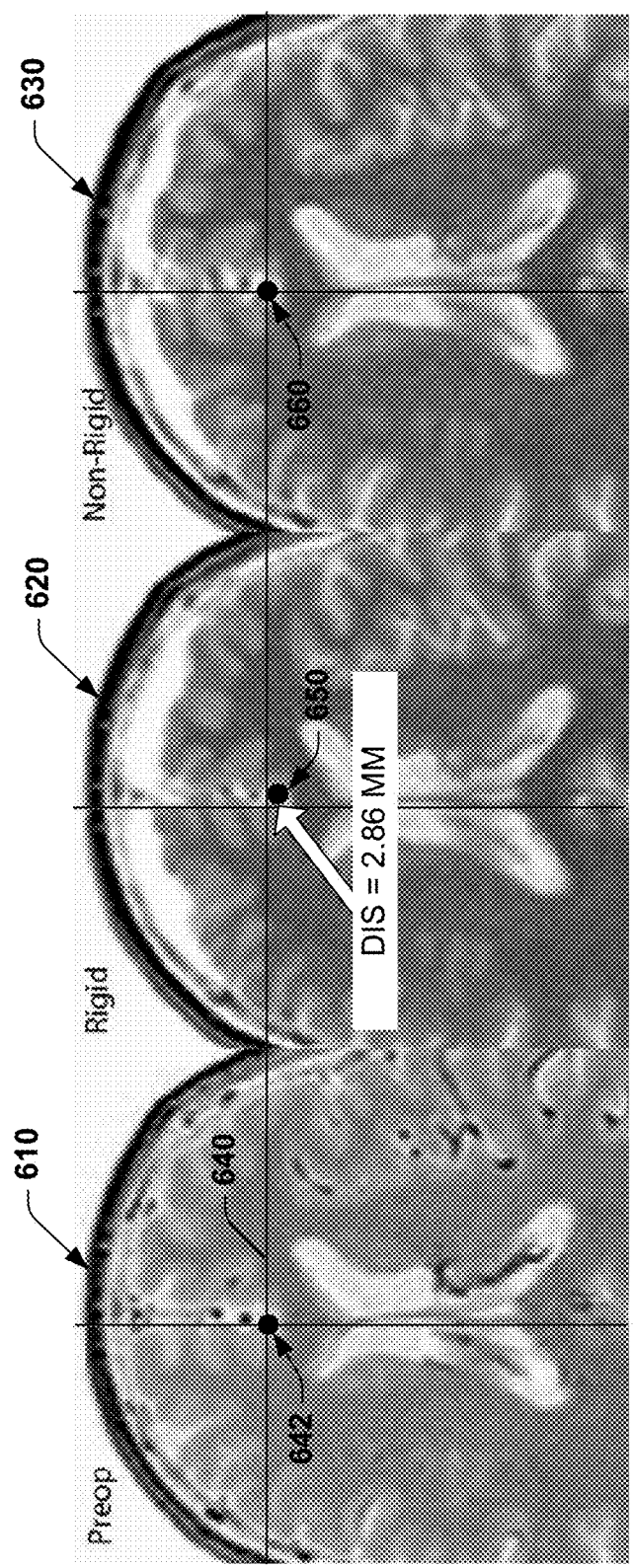
FIG. 6 illustrates example images of a preoperative image, a rigidly aligned image, and a non-rigidly aligned image.

FIG. 6 illustrates three example images where a preoperative image is shown at 610, a rigidly aligned image at 620, and a non-rigidly registered image at 630. A measuring crossbar 640 represents a location of a selected feature 642 in the preoperative image 610. At 620, after rigid alignment between the preoperative image 610 and a postoperative image having a deformation bubble, the measuring crossbar 642 shows a downward vertical displacement of about 2.86 mm at 650. At 630, after non-rigid alignment between the preoperative image 610 and a postoperative image having a deformation bubble, the measuring crossbar 642 shows that the displacement of about 2.86 mm at 650 has been removed at 660. Thus, a mapping can then be performed to generate displacement data describing how the preoperative feature shown at 642 has been displaced (e.g., magnitude and direction) based on the rigid alignment and the non-rigid alignment depicted at one point at 660.

FIG. 7 illustrates an example method 700 for performing displacement mapping via rigid and non-rigid registration for different images acquired for a common anatomical structure of a given patient. For example, the images could be pre-operative and post-operative images or any images in which one of the images exhibits localized deformation of an anatomical region, such as disclosed herein. At 710, the method 800 includes accessing image data from memory that includes a first image of an anatomical feature and a second image of the anatomical feature. The image modalities used to acquire the images can be the same or different. The images can be two-dimensional or three-dimensional images. At 720, the method 700 includes performing a rigid alignment between the preoperative image and postoperative image to generate a rigidly aligned image (e.g., via fusion engine 110 of FIG. 1 or fusion engine 500 and rigid alignment 510 of FIG. 5). At 730, the method 700 includes performing a non-rigid registration between the rigidly aligned image and the first image (e.g., via fusion engine 500 and non-rigid alignment 520 of FIG. 5). At 740 of FIG. 7, the method 700 includes generating a vector field mapping based on the non-rigid alignment to provide displacement data regarding displacement between the preoperative image and the postoperative image (e.g., via fusion engine 500 and mapping tool 560 of FIG. 5). The displacement data can include a magnitude and direction that quantifies the deformation for each common pixel or voxel in the images accessed at 710.

Although image alignment between preoperative and post-operative images which includes intraoperative images can involve first a rigid alignment between images followed by a non-rigid alignment, it is possible that a non-rigid registration can be performed without first performing the rigid alignment described at 830. For example, after acquiring the preoperative image (e.g., of a patient's brain) as the first image and an intraoperative or postoperative image of the same brain in roughly the same orientation (second image), the method 800 can perform a three-dimensional non-rigid registration of the second image to the first image. This non-rigid registration can be analyzed to calculate a three-dimensional vector field for which each point in the field indicates the direction and distance from a location in the second image to the corresponding location in the first image.

The vector field can then be employed to provide feedback to a user (e.g., surgeon, other software, robot, medical device, and so forth) indicating compensation (e.g., distance, trajectory) required to target a specific preoperatively identified structure, or inversely to predict the equilibrium location of an intraoperatively/postoperatively identified structure. For example, the displacement data can be further mapped into three-dimensional coordinate system of the patient (e.g., a stereotactic coordinate system) that can be utilized to in a subsequent surgical procedure to accurately access a target site in the deformed anatomical structure. As noted above, a model can be developed to predict how a structure might continue to move over time which can also be employed to update the feedback to the user.

As a further example, if a rigid alignment is employed before the non-rigid registration then the method 700 can first convert the first image and the second image to format utilized by the fusion engine. This can include pre-processing between the images, such as can include cropping the first image and second image and performing background removal to remove unnecessary data and decrease alignment time, for example. After any pre-processing that may occur, the method 800 can then perform rigid-registration of the second image to first image. This can be achieved using a Normalized Mutual Information correlation metric with Gradient Descent optimization and Linear interpolation, for example. After the rigid registration, perform the non-rigid-registration of the aligned second image to first image. This can also be achieved using a Normalized Mutual Information correlation metric with Gradient Descent optimization and Linear interpolation, for example. Other optimization techniques could be utilized for the rigid alignment and non-rigid registration. Non-rigid registration typically first divides the images into a lattice/grid, then iteratively evaluates and optimizes correlation metrics for each cell in the lattice using intermediate results to adjust a continuous nonlinear mapping (vector field) between the second and first image, which is in turn used to generate the correlation metric. The aligned image and vector field can then be employed as inputs to provide guidance regarding deformation and associated displacement between the respective images.

Figure 8:
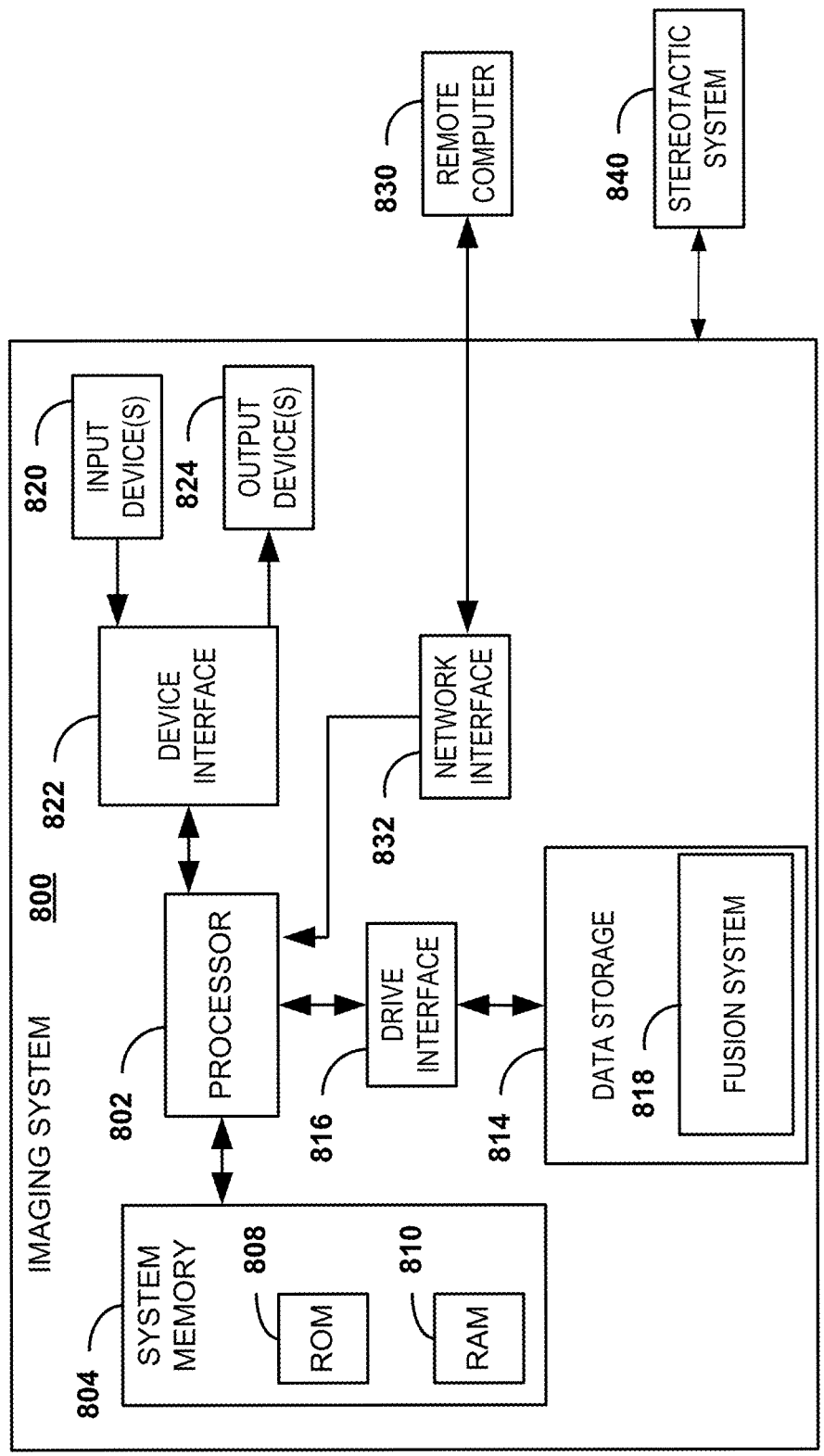
FIG. 8 illustrates an example system for performing fusion with compensation for brain deformation.

FIG. 8 illustrates an example system 800 for performing fusion with compensation for brain deformation in accordance with an aspect of the present invention. The system 800 can include one or more general purpose networked computer systems, embedded computer systems, routers, switches, server devices, client devices, various intermediate devices/nodes, and/or stand alone computer systems (desktop or portable).

The system 800 includes a processor 802 and a system memory 804. Dual microprocessors and other multi-processor architectures can also be utilized as the processor 802. The processor 802 and system memory 804 can be coupled by any of several types of bus structures, including a memory bus or memory controller, a peripheral bus, and a local bus using any of a variety of bus architectures. The system memory 804 can include read only memory (ROM) 808 and random access memory (RAM) 810 as well as any other non-transitory computer readable media that can store data and instructions executable by the processor 802. A basic input/output system (BIOS) can reside in the ROM 808, generally containing the basic routines that help to transfer information between elements within the system 800, such as a reset or power-up.

The system 800 can employ one or more types of non-transitory data storage 814, including a hard disk drive, a magnetic disk drive, (e.g., to read from or write to a removable disk), solid state memory (e.g., flash drive) and an optical disk drive, (e.g., for reading a CD-ROM or DVD disk or to read from or write to other optical media). The data storage can be connected to the processor 802 by a drive interface 816. The data storage 814 thus can store instructions executable by the processor 802 and related data for the computer system 800. A number of program modules may also be stored in the data storage 814 as well as in the system memory 804, including an operating system, one or more application programs, other program modules, and program data. In the example of FIG. 8, the data storage 814 can include a fusion system 818 (e.g., the system 100 of FIG. 1 or the system 500 of FIG. 5) that is programmed to perform clinical imaging fusion. Such executable instruction can be executed by the processor 802, such as when loaded from the RAM 810.

A user may enter commands and information into the computer system 800 through one or more input devices 820, such as a keyboard, a touchscreen, physiologic input devices, biomarker readers, photo devices and scales, card scanners, and/or a pointing device (e.g., a mouse). It will be appreciated that the one or more input devices 820 can include one or more physiologic sensor assemblies transmitting data to the system 800 for further processing. These and other input devices are often connected to the processor 802 through a device interface 822. For example, the input devices can be connected to the system bus by one or more a parallel port, a serial port or a USB. One or more output device(s) 824, such as a visual display device or printer, can also be connected to the processor 802 via the device interface 822.

The system 800 may operate in a networked environment using logical connections (e.g., a local area network (LAN) or wide area network (WAN)) to one or more remote computers 830. A given remote computer 830 may be a workstation, a computer system, a router, a peer device, or other common network node, and typically includes many or all of the elements described relative to the computer system 800. The system 800 can communicate with the remote computers 830 via a network interface 832, such as a wired or wireless network interface card or modem. In a networked environment, application programs and program data depicted relative to the system 800, or portions thereof, may be stored in memory associated with the remote computers 830.

Additionally, as disclosed herein the system 800 can be communicatively coupled (e.g., directly or via a network connection) with a stereotactic system 840. The stereotactic system can employ a resulting brain atlas and/or displacement data for performing a stereotactic procedure. For example, a mathematical model corresponding to the brain atlas can be provided and converted to a three-dimensional coordinate system of the stereotactic system 840 via an appropriate transform. The resulting atlas or other displacement data thus can be utilized to facilitate manual or automated (e.g., robotic) surgery relative to an identified target site in the brain. As another example, a user can select a target site in a pre-deformation image (e.g., a preoperative image) and the fusion system 818 can be configured to identify the current three-dimensional location in a coordinate system of the stereotactic system 840. The fusion with the brain atlas enables a more accurate identification of the target site as it accounts for deformation as disclosed herein.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system, comprising:
    a model to represent a volumetric deformation of a brain, stored in a memory, corresponding to brain tissue that has been displaced or shifted by at least one of disease, surgery or anatomical changes; and a fusion engine, executed by a processor, to employ the model to perform a coarse fusion to align a first three-dimensional image of a patient's brain with respect to a second three-dimensional image of the patient's brain after a region of the brain has been displaced or shifted,
    wherein the coarse function comprises:
        determining an initial volume of at least one selected anatomic region in the first three-dimensional image of the patient's brain and another volume of the at least one selected anatomic region in the second three-dimensional image of the patient's brain;
        computing shrinkage or growth factors from the first three-dimensional image of the patient's brain based on a difference between the initial volume and the another volume for the at least one selected anatomic region;
        generating a mapping between the first and second three-dimensional images of the patient's brain based on the computed shrinkage or growth factors and at least one volume parameter of the model to provide feedback that compensates for distortion between the first and second three-dimensional images of the patient's brain; and
        adjusting one or more points on a displacement vector of the model extending through the at least one selected anatomic region to compensate for spatial deformations that occur between the first and second image of the patient's brain based on the mapping.

2. The system of claim 1, further comprising a fiducial marker in the first three-dimensional image of the patient's brain, the fusion engine being programmed to employ the fiducial marker with the volumetric analysis of the model and apply to the first three-dimensional image of the patient's brain to compensate for distortion in the first three-dimensional image of the patient's brain for at least one spatial region of interest selected in response to a user input.

3. The system of claim 2, wherein the fiducial marker is selected in the first three-dimensional image of the patient's brain in response to a user input or an automated system.

4. The system of claim 1, wherein the brain image includes at least one landmark or fiducial marker, the fusion engine is programmed to apply the volumetric analysis of the model and the at least one landmark or fiducial marker to the first three-dimensional image of the patient's brain to compensate further for distortion in the first three-dimensional image of the patient's brain in relation to at least one other image.

5. The system of claim 1, wherein the fusion engine is programmed to fuse or co-register the first three-dimensional image of the patient's brain with the second three-dimensional image of the patient's brain based on the model.

6. The system of claim 5, wherein the model and the fusion engine are employed to fuse or co-register the second three-dimensional image of the patient's brain with a brain atlas to provide an adjusted brain atlas.

7. The system of claim 6, further comprising a vector calculator configured to determine a displacement vector for each pixel or voxel in the second three-dimensional image of the patient's brain and transform each pixel or voxel into a coordinate system of a stereotactic system.

8. The system claim of 7, wherein the fusion engine processes at least one image event that includes at least one of a location of a fiducial marker, a foreign body inserted in the patient's brain, and an anatomical structure after anatomical displacement.

9. The system of claim 8, wherein the image event is correlated or co-registered with a corresponding location in images acquired before the anatomical displacement occurred or after the anatomical displacement has resolved partially or completely.

10. The system claim of 9, wherein the fusion engine compensates for a structural shift that includes a brain shift associated with surgical procedures.

11. A method comprising:
performing a non-rigid alignment between the first three-dimensional image data and the second three-dimensional image data comprising:
determining an initial volume for at least one selected anatomic region in a first three-dimensional brain image for a patient;
determining another volume for the at least one selected anatomic region in a second three-dimensional brain image for the patient;
computing shrinkage or growth factors from the first three-dimensional brain image based on a difference between the initial volume and the another volume for the at least one selected anatomic region; and
generating a mapping between the first and second three-dimensional brain images based on the computed shrinkage or growth factors and at least one volume parameter for the brain to provide feedback that compensates for distortion between the first and second three-dimensional brain images; and
generating a vector field mapping based on the non-rigid alignment to provide displacement data to a user regarding displacement between the first image data and the second image data.

12. The method of claim 11, wherein the at least one selected anatomic region comprises at least one of a ventricular region, a subarachnoid region, a cortical region and a subcortical region.

13. The method of claim 11, further comprising utilizing one or more fiducial markers or landmarks to characterize inhomogeneities in anatomy or inhomogeneities in a vector of displacement and align images from a digitized atlas and a brain image.

14. A method, comprising:
accessing a first three-dimensional image data of an anatomical feature for a patient and second three-dimensional image data of the anatomical feature for the patient;
performing a non-rigid alignment between the first three-dimensional image data and the second three-dimensional image data comprising:
determining an initial volume for at least one selected anatomic region in the first three-dimensional image data and determining another volume for the at least one selected anatomic region in the second three-dimensional image data;
computing a shrinkage or growth factor from the first three-dimensional brain image based on a difference between the initial volume and the another volume for the at least one selected anatomic region; and
generating a mapping between the first and second three-dimensional image data based on the computed shrinkage or growth factors and at least one volume parameter for the brain to provide feedback that compensates for distortion between the first and second three-dimensional image data; and
generating a vector field mapping based on the non-rigid alignment to provide displacement data to a user regarding displacement between the first image data and the second image data.

15. The method of claim 14, further comprising performing a rigid alignment between the first image data and the second image data to generate a rigidly aligned image.

16. The method of claim 15, wherein the rigid alignment or the non-rigid alignment includes at least one of a normalized mutual information correlation metric, a gradient descent optimization, and a linear interpolation between images.

17. The method of claim 16, wherein the non-rigid registration divides the images into a lattice and iteratively evaluates and optimizes correlation metrics for each cell in the lattice.

18. The method of claim 16, wherein the non-rigid registration employs intermediate results to adjust a continuous nonlinear mapping between the first image data and the second image data which is used to generate the correlation metrics.

19. The method of claim 14, further comprising generating a model which describes how the anatomical feature shifts over time and employing the model to update the vector field mapping over time.

* * * * *